United States Patent [19]

Paton

[11] 4,429,043

[45] Jan. 31, 1984

[54] ANAEROBIC DIGESTION OF ORGANIC WASTE FOR BIOGAS PRODUCTION

[75] Inventor: Robert Paton, Ponce, P.R.

[73] Assignee: Biorganic Energy Inc., Hato Rey, P.R.

[21] Appl. No.: 337,250

[22] Filed: Jan. 5, 1982

[51] Int. Cl.³ .............................................. C12P 5/02
[52] U.S. Cl. .................................. 435/167; 435/801; 71/10; 210/603; 426/55
[58] Field of Search ................. 435/801, 167, 813; 210/603, 218, 613, 320; 48/197 A, 197 FM; 426/55, 56; 71/10

[56] References Cited

U.S. PATENT DOCUMENTS

| | | | |
|---|---|---|---|
| 836,386 | 11/1906 | Keegan | 210/320 |
| 1,930,457 | 10/1933 | Pruss | 210/613 |
| 1,990,523 | 6/1932 | Buswell et al. | |
| 2,202,772 | 5/1940 | Durdin | 210/603 |
| 2,331,031 | 10/1943 | Kurtz | 210/603 X |
| 2,429,589 | 10/1947 | Wiley | 435/167 |
| 2,458,431 | 1/1949 | Schlenz | 210/603 X |
| 2,528,649 | 11/1950 | Genter et al. | 210/603 X |
| 2,640,027 | 5/1953 | McNamee et al. | 210/603 |
| 2,889,929 | 6/1959 | Kinell | 210/603 X |
| 2,893,957 | 7/1959 | Genter et al. | 210/603 |
| 3,242,055 | 3/1966 | DeLucia | 210/603 X |
| 3,383,309 | 5/1968 | Chandler | |
| 3,768,200 | 10/1973 | Klock | 210/603 |
| 3,925,208 | 12/1975 | Yost | 210/320 X |
| 3,973,043 | 8/1976 | Lynn | |
| 4,022,665 | 5/1977 | Ghosh et al. | |
| 4,100,023 | 7/1978 | McDonald | |
| 4,204,842 | 5/1980 | Morel et al. | 435/167 X |
| 4,252,901 | 2/1981 | Fischer et al. | 210/603 X |
| 4,274,838 | 6/1981 | Dale et al. | |
| 4,329,428 | 5/1982 | Ghosh et al. | 435/167 |
| 4,334,997 | 6/1982 | Peterson | 210/603 X |
| 4,342,568 | 8/1982 | Taniguchi | 210/603 X |
| 4,374,199 | 2/1983 | Carter | 210/603 X |
| 4,375,412 | 3/1983 | Schimel | 210/603 |

*Primary Examiner*—R. B. Penland
*Attorney, Agent, or Firm*—Roylance, Abrams, Berdo & Goodman

[57] ABSTRACT

A low solids aqueous suspension of organic waste is treated in at least four, e.g., six serial anaerobic zones at a temperature of less than 40° C. and under quiescent conditions to provide methane, fertilizer and a clean liquid effluent.

16 Claims, 3 Drawing Figures

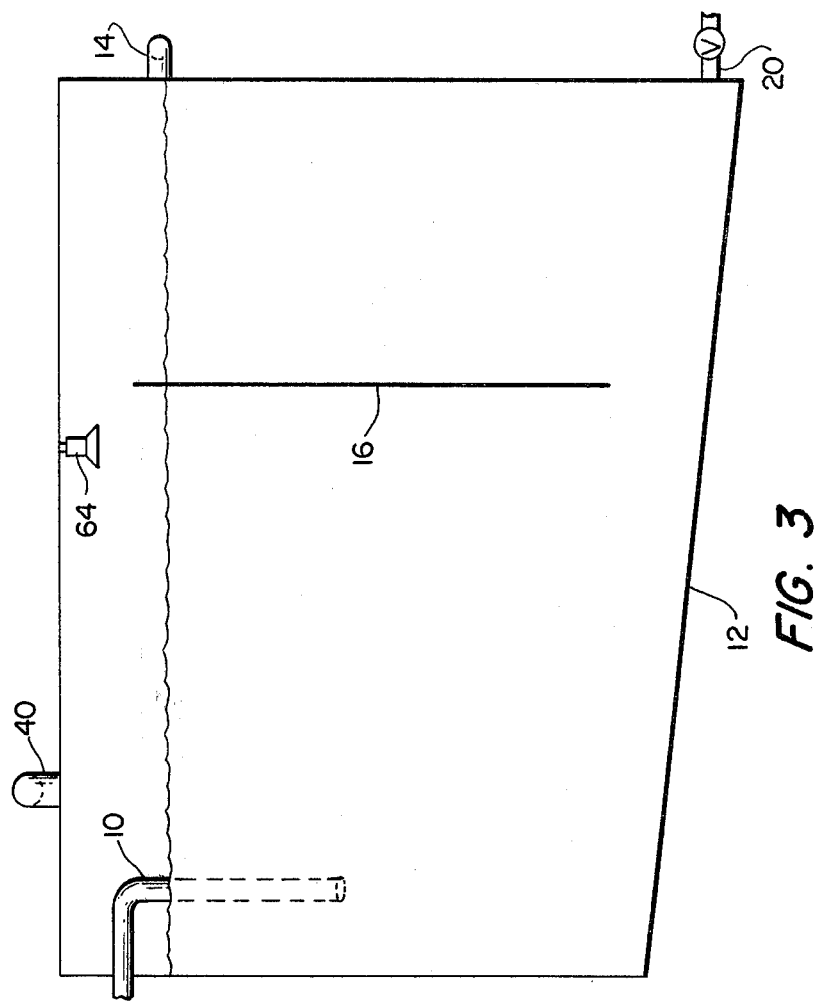
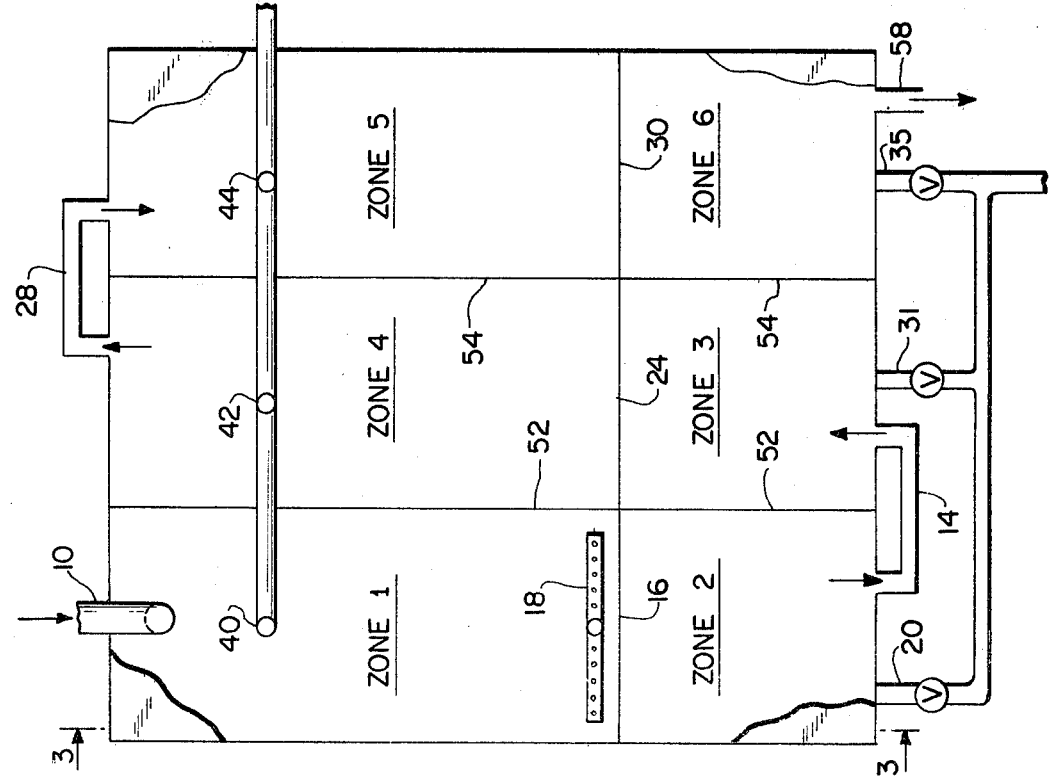

ANAEROBIC DIGESTION OF ORGANIC WASTE FOR BIOGAS PRODUCTION

BACKGROUND OF THE INVENTION

This invention relates to a process for converting organic waste material into methane and other useful products such as fertilizer. More specifically, this invention relates to an anaerobic digestion process which is conducted in several zones.

Organic waste such as straw, paper and particularly animal wastes, i.e., manure, have long been considered a potential resource for the production of methane gas. Substantial amounts of money and effort have been directed towards providing a practical process for utilization of this resource. Typical methods involve both aerobic and anaerobic degradation of the waste within a complex system.

Most prior art systems involve treating an aqueous suspension of the waste having a solids content of about 10% or greater in a fermentative system which requires heating of at least part of the system. Such systems also typically require intermittent or continuous mixing and frequent periodic maintenance. Recirculation of microbe-rich or activated sludge is often an essential part of the system and operation normally requires nontrivial technological expertise. Initial capital investment to acquire such systems is generally prohibitive.

SUMMARY OF THE INVENTION

A simple and economical process for the conversion of organic waste material and particularly animal wastes into substantial amounts of methane has now been found. The process can be operated with little or no expertise and requires little or no maintenance. In accordance with the invention, organic waste material is anaerobically treated. A low solids aqueous suspension of organic waste is periodically passed into the first of at least four, e.g., six serially arranged anaerobic zones. The zones communicate with one another in a manner such that addition of liquid to the first zone, when six zones are employed, causes: liquid flow from the lower portion of the first anaerobic zone to the lower portion of the second anaerobic zone; liquid flow from the upper portion of the second anaerobic zone to the upper portion of the third anaerobic zone; liquid flow from the lower portion of the third anaerobic zone to the lower portion of the fourth anaerobic zone; liquid flow from the upper portion of the fourth anaerobic zone to the upper portion of the fifth anaerobic zone; liquid flow from the lower portion of the fifth anaerobic zone to the lower portion of the sixth anaerobic zone; and liquid flow out of the upper portion of the sixth anaerobic zone. Such serial liquid communication constitutes the only liquid communication between these zones. All of the zones are maintained at substantially quiescent conditions. This provides three vertically arranged strata in at least each of the first four zones. The upper stratum includes an aqueous suspension of lignocellulosic solids. The intermediate stratum includes an aqueous solution of acids which are predominantly medium length fatty acids such as valeric and propionic acids. The lower stratum includes an aqueous solution of acids which are predominantly formic and acetic acids. Each of the zones is maintained at an ambient temperature that can range from 26° to 34° C., thus the system normally needs no energy input unless faster degradation is required in which case the temperature can be increased up to 40° C. in the first zone only. Methane gas is collected from the top of the zones and fertilizer solids can be periodically removed from a lower portion of the zones 2, 3 and 6. The liquid effluent removed from the sixth zone requires little or no further treatment to meet environmental standards.

BRIEF DESCRIPTION OF THE DRAWINGS

In the drawings which form part of the original disclosure of the invention:

FIG. 2 is a top plan view shown in partial cutaway and illustrates one preferred arrangement of the various zones; and FIG. 3 is a side view of the arrangement shown in FIG. 2, taken at line 3—3.

DETAILED DESCRIPTION OF THE INVENTION

Figure 1:
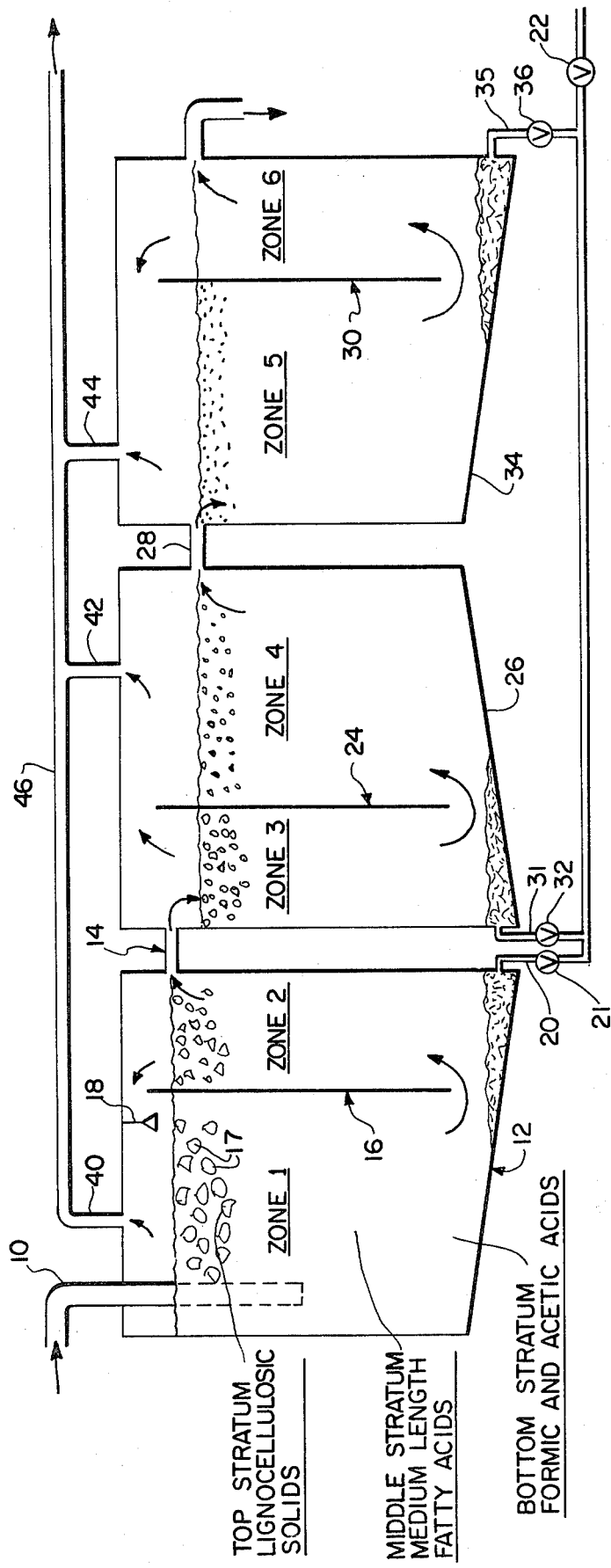
FIG. 1 is a flow diagram illustrating one preferred embodiment of the invention.

FIG. 1 diagrammatically illustrates one advantageous embodiment of the method. A low solids aqueous suspension of organic waste is periodically passed via line 10 into zone 1. The organic waste can be straw, paper or other lignocellulosic material and is advantageously an animal waste, i.e., manure. The solids will constitute less than about 4% by weight of the aqueous suspension added by line 10 and are preferably less than 3% by weight, most preferably about 2% by weight. The size of the first zone is dependent upon the BOD and/or COD content of the material which is to be treated in the process. There should be sufficient liquid space in the first zone that there is at least 10 gallons of liquid space per pound of BOD or COD which is added to the system in any eight hour period. The liquid depth of zone 1, which is determined by the bottom of zone 12 and the location of exit pipe 14, should be within the range of about 10 to about 30 feet, preferably between about 10 and about 18 feet in order to provide stratification in the zone and to allow methogenic bacteria to flourish.

Zone 1 is defined by side walls (not shown), a front wall and baffle 16 which extends the width of the entire zone, i.e., from side wall to side wall. The height of the baffle is adjusted so that it terminates at the top at least about 10 inches above the water level which is defined by pipe 14. The top of the baffle preferably terminates below the roof of the zone so that there is gaseous communication between zones 1 and 2. The bottom of the baffle should terminate prior to contacting the floor of the zone so that there is liquid communication between the bottom of zone 1 and the bottom of zone 2. The space between the bottom of the baffle and the bottom of the zone should be about 30 inches, but this can vary to provide a bottom space having a height of from about 18 inches to about 48 inches.

An important aspect of the invention is that the liquid-solid mixture in the zones is maintained under substantially quiescent or undisturbed conditions. This promotes stratification of the mixture. A top layer which can have a depth of up to about two feet will be floating lignocellulosic solids, 17. As anaerobic bacteria degrade this material, medium length fatty acids such as valeric, butyric and propionic acids are formed and these will be located predominantly as an intermediate layer in the zone. As these intermediate acids are degraded, formic and acetic acids are formed and will be located in the bottom stratum of the zone. Methane and carbon dioxide are formed from the bacterial degradation of these simple acids in the bottom of the zone.

To maintain quiescense, it is necessary that the solid-liquid suspension added via line 10 to zone 1, be added in a manner so that the force of entry is relatively low. This is partially accomplished by submerging the entry pipe 10 into the liquid in the first zone to a depth which is below the level of floating solids, e.g., about five feet. Additionally, the diameter of the entry pipe should be large, thus assuring that the force of the entering material will be spread over a larger area.

Sprinkler 18 is provided at a location close to the baffle. Water pressure and the design of the sprinkler are adjusted so that water issuing from the sprinkler will merely wet floating solids and cause no turbulence. Depending on temperature, location and the particular organic waste, it is possible that the uppermost portion of the floating organic wastes 17 will form a dry, hard, matted layer and will not be acted upon by bacteria. Accordingly, a sprinker such as 18 can be provided to wet the floating wastes causing at least some to gently sink, thus causing the hardened mat of solids to be broken.

The bottom floor 12 of zone 1, or as shown in FIG. 1, zones 1 and 2, is preferably sloped in a direction away from the entering materials. Such slope can be varied as desired and it has been found that a slope of about 7° is suitable. Some degraded solids will sink to the bottom of the zone and flow down the slope. These solids can be removed periodically via line 20 by opening valves 21 and 22 and are useful as fertilizer. When too great an amount of solids have accumulated on the floor of the tank there will be a noticeable decrease in methane production. Solids should be removed via line 20 at that time. The solids have little malodorous quality when fully degraded. When solids which have not been fully degraded are allowed to pass out of the system, a highly noticeable and aromatic smell of organic acids will be apparent and at this point valves 22 and 21 should be closed.

Zone 2 is preferably of a size which is about one-half the size of zone 1. Thus, when zones 1 and 2 are located in a single tank as shown in FIG. 1, zone 2 should constitute about one-third the length of the tank. The upper portion of zone 2 communicates with the upper portion of zone 3 via line 14. It is preferred that the water level in zone 3 be somewhat lower, e.g., about 10 inches, than the water level in zone 2. This insures that materials passing via pipe 14 from zone 2 to zone 3 will drop as they pass out of pipe 14 and will be submerged. Thus the floating solid will be wetted upon entry into zone 3.

The size of zone 3 is preferably about the same size as zone 2. The location and spacing of baffle 24, between zones 3 and 4, is about the same as between zones 1 and 2. However, the size of zones 3 and 4 can be varied, as desired, so long as the bottoms of the zones communicate from one to the other. As indicated previously, the size of zones 1 and 2 is most important to proper operation of the process.

The bottom of zone 3 communicates with the bottom of zone 4 beneath the bottom of baffle 24 which, as with baffle 16, is preferably spaced about 30 inches from the bottom 26 of zones 3 and 4. The top of zone 4 communicates via line 28 with the top of zone 5. Zone 5 communicates with zone 6 via the space underneath baffle 30 which is arranged preferably in the same manner as baffles 24 and 16.

The direction of the slope of the bottom 26, of zones 3 and 4 can be in any direction desired. It is preferred that there be some slope to facilitate removal of solids via line 31 and valve 32 as shown. Likewise, the direction of slope of the bottom 34, of zones 5 and 6 can be as desired and the slope facilitates removal of solids via line 35 and valve 36.

It will be appreciated that as material passes through the serial zones, a greater amount of degradation takes place. By maintaining quiescent conditions in all zones, there will be strata formed in all zones. The amount of solids passing through zones 1, 2, 3 and 4 will be such that there will be a layer of solids in each of the zones. By the time the material reaches zones 5 and 6, there may be little, if any, floating solids. However, even in these zones there will be acid strata. In most cases, there will be floating solids also in zone 5 and a small amount of solids in zone 6.

Methane is collected from the zones via lines 40, 42 and 44 and is passed via line 46 to storage. The gas can be stored in any conventional system or manner. One preferred method of storage is through the use of a water sealed gas holder in which the gas is collected beneath a tank floating in water. Such water sealed gas holders are known to those skilled in the art. By using such a system, there is a continuous back pressure kept on the gas which is preferably about 0.4 psi above atmospheric pressure. This causes some gases to be redissolved in the system and is believed to promote the growth of various bacteria. If the gas is collected by means of a system other than a water sealed gas holder, back pressure in the system can be effected by means known to those skilled in the art such as through the use of a pressure reduction valve provided in line 46. The stored gas can be used as desired to provide useable energy, e.g., in the form of electricity.

The system is maintained at ambient temperature and in many areas of the world will need no added heat. This is because the system has been designed to utilize mesophilic, methogenic bacteria. It is preferred that the system be operated at a temperature of from about 26° C. to about 40° C, and more preferably at a temperature of less than 32° C. It has been found that best results are obtained when the system is operated at a temperature of between 26° and 30° C. When it is desired to operate the system in a colder climate, heat may be provided by any conventional means. One contemplated method of providing heat under such circumstances is to locate the system within an insulated structure wherein a space is provided between the outer walls of the zones and the inner walls of the insulated structure. Exhaust gas from generators used to convert the methane into electricity can then be passed into this space and the waste heat thus efficiently utilized to heat the system.

One preferred arrangement of the various zones is shown in FIGS. 2 and 3. Zones 1 and 4, and 2 and 3 share a common side wall 52. Zones 4 and 5 and 3 and 6 likewise share a common side wall 54. Baffles 16, 24 and 30 extend from side to side of the zones and are located in a coplanar arrangement. Material is admitted to the first zone via line 10. Sprinkler 18 is located close to baffle 16 and above zone 1 for intermittently wetting floating material as necessary. Materials pass beneath baffle 16 and out of the upper portion of zone 2 via line 14 whereupon they enter into the upper portion of zone 3. Materials are then passed beneath baffle 24 and exit from the upper portion of zone 4 via line 28. Finally, materials pass beneath baffle 30 and then exit the system via line 58.

The diameters of pipes 14, 28 and 58 can be varied to help maintain the quiescent conditions in the zones. Thus, the diameter of such pipes should be large enough that they will not be clogged by solid material passing through them; also, by keeping the diameter relatively large, the flow of material from zone to zone will be slowed so as not to cause excess turbulence. It has been found that a diameter of about six inches is the smallest suitable diameter. This can be varied as desired and depending upon types of solids treated, and the like.

Solids are removed from the bottom of the zones via lines 20, 31 and 35 while the methane gas is collected via lines 40, 42 and 44. The advantageous layout of the system shown in FIGS. 2 and 3 is such that it forms a single modular unit. The slope of the bottom of the unit 12 can advantageously be in a single direction.

It has been found that certain inorganic chemicals can dramatically improve operation of the system. Thus, the addition of sulfate as copper sulfate is recommended in an amount of between about 1 and about 1½ pounds, based on 10,000 gallons, added at intervals of two to three weeks. Iron, in the form of the metal, can be added in an amount of about one ton, based on 230,000 gallons, at a period of about once every two to three years. Molybdenum, added in the form of soluble molybdenum, is added in an amount of between 2 to 3 pounds, based on about 700,000 gallons, every two to three years.

It is believed that the quantity of the methane gas produced can also be increased by recirculating the total gas produced through the last four stages of the series of zones, thereby increasing the amount of dissolved $CO_2$ which has a favorable effect upon the metabolism of the methogenic bacteria in these stages. Recirculation of the gas can be accomplished by inserting a pipe at a distance of about two feet from the bottom of each of the last four zones and gently circulating gas into the zone through such pipes.

The following example illustrates operation and practice of the invention and constitutes the best mode.

EXAMPLE

A fermentation system such as illustrated in FIGS. 1, 2 and 3, together with a biogas storage system, a generating plant and an effluent holding tank were installed on a pig farm having approximately 2,000 pigs. Wastes were pressure washed from the pens twice and passed by gravity flow into the first zone of the digestor. The digestor constituted three tanks, sharing two common walls as shown in FIG. 2 and had a total liquid capacity of about 700,000 gallons. The capacity of such tanks was designed based on a future expectation of about 11,000 animals. The overall length of the tank was 96 feet, and the liquid depth within the tanks was 11 feet at the entrance end and 17 feet at the exit end. The solids constituted 2% of the liquid solid suspension added twice daily to the tanks. The system was operated for six months without removal of solids in order to increase the solid concentration within the system which was required for the efficient operation of the system. Thereafter, solids were removed every 21 days and were used as fertilizer.

Copper sulfate in an amount of approximately 1 lb./10,000 gallons was added periodically every two to three weeks, scrap iron weighing about three tons was added once and molybdenum in an amount of two pounds was added once. The system generated about 10,000 to 11,000 cubic feet of gas per day of which 75% constituted methane gas. The remainder was carbon dioxide. Electricity was generated and used at the farm in an amount of about 600 kilowats per day.

Measurements of BOD and COD were taken of material entering the system and material exiting the system and it was found that BOD and COD had been reduced by 90–95%.

In order to more fully study operation of the system, BOD and COD contents were measured at the following locations:

Location 1: Solids/liquid suspension prior to introduction into system
Location 2: Upstream end of zone 1
Location 3: Downstream end of zone 1
Location 4: Downstream end of zone 2
Location 5: Upstream end of zone 3
Location 6: Downstream end of zone 4
Location 7: Upstream end of zone 5
Location 8: Downstream end of zone 5
Location 9: Downstream end of zone 6
Location 10: Effluent pipe exiting zone 6

The following results were obtained:

| Location Number | BOD[a] (mg/l) | COD[b] (mg/l) | BOD/COD rates |
|---|---|---|---|
| 1 | 2389 ± 241 | 6352 ± 742 | 0.36:1 |
| 2 | 480 ± 42 | 1807 ± 92 | 0.27:1 |
| 3 | 443 ± 40 | 1999 ± 88 | 0.22:1 |
| 4 | 421 ± 40 | 2090 ± 102 | 0.20:1 |
| 5 | 212 ± 22 | 860 ± 52 | 0.25:1 |
| 6 | 220 ± 33 | 840 ± 53 | 0.26:1 |
| 7 | 147 ± 16 | 599 ± 39 | 0.25:1 |
| 8 | 141 ± 13 | 584 ± 43 | 0.24:1 |
| 9 | 143 ± 18 | 584 ± 43 | 0.24:1 |
| 10 | 141 ± 16 | 576 ± 46 | 0.24:1 |

[a] Mean ± standard error; 11 N 16 observations per value.
[b] 10 N 15 observations per value.

It can be seen that total BOD and COD reduction was in excess of 90%. Further, since reduction in BOD and COD is directly proportional to the amount of methane gas produced, the above table indicates the relative amounts of methane produced in each of the various zones.

Although the invention has been described in detail with reference to preferred embodiments, variations and modifications can be made without departing from the invention as described in the foregoing specification and defined in the appended claims. Thus, while the system has been specifically described using six anaerobic zones, the number of zones can be reduced to four if COD loads are not very large by eliminating baffles 24 and 30 in the second and third tanks.

What is claimed is:

1. An anaerobic bacterial process for converting manure containing organic waste material into methane and fertilizer, the combination of steps consisting essentially of:

passing a low solids aqueous suspension of manure containing organic wastes having a solids content of less than about 4% by weight into the first of at least four anaerobic zones, the first and second anaerobic zones being located in one tank and the third and fourth anaerobic zones being located in a second tank, the second zone having a liquid space about one half the liquid space of the first zone, said zones being arranged for liquid communication in series such that addition of liquid to the first zone causes;
  liquid flow from the lower portion of the first anaerobic zone to the lower portion of the second anaerobic zone;
  liquid flow from the upper portion of the second anaerobic zone to the upper portion of the third anaerobic zone;
  liquid flow from the lower portion of the third anaerobic zone to the lower portion of the fourth anaerobic zone;
  liquid flow out of the upper portion of the last anaerobic zone;
said serial liquid communication being the only liquid communication between zones, there being no passing of the settled solids from the second anaerobic zone to the third anaerobic zone,
maintaining quiescent conditions in each of said anaerobic zones whereby a three layer stratification of the mixture occurs,
maintaining ambient temperature of up to about 40° C. in each of said zones; and
collecting methane from the top of said zones and periodically removing fertilizer solids from said zones.

2. An anaerobic bacterial process for converting manure containing organic waste material into methane and fertilizer, the combination of steps consisting essentially of:
  passing a low solids aqueous suspension of manure containing organic wastes having a solids content of less than about 4% by weight into the first of six anaerobic zones, the first and second anaerobic zones being located in one tank, the third and fourth anaerobic zones being located in a second tank and the fifth and sixth anaerobic zones being located in a third tank, the second zone having a liquid space about one half of the liquid space in the first zone, said zones being arranged for liquid communication in series such that addition of liquid to the first zone causes;
  liquid flow from the lower portion of the first anaerobic zone to the lower portion of the second anaerobic zone;
  liquid flow from the upper portion of the second anaerobic zone to the upper portion of the third anaerobic zone;
  liquid flow from the lower portion of the third anaerobic zone to the lower portion of the fourth anaerobic zone;
  liquid flow from the upper portion of the fourth anaerobic zone to the upper portion of the fifth anaerobic zone;
  liquid flow from the lower portion of the fifth anaerobic zone to the lower portion of the sixth anaerobic zone; and
  liquid flow out of the upper portion of the sixth anaerobic zone,
said serial liquid communication being the only liquid communication between zones, there being no passing of settled solids from the second anaerobic zone to the third anaerobic zone or from the fourth anaerobic zone to the fifth anaerobic zone,
maintaining quiescent conditions in each of the six anaerobic zones whereby a three layer stratification of the mixture occurs,
maintaining ambient temperature of up to about 40° C. in each of said zones; and collecting methane from the top of said zones and periodically removing fertilizer solids from a lower portion of three of said zones.

3. The process of claims 1 or 2 wherein said quiescent conditions provide in each of the first four zones, said three layer strata which are:
  an upper stratum comprising an aqueous suspension of lignocellulosic solids,
  an intermediate stratum comprising an aqueous solution of acids which are predominantly medium length fatty acids; and
  a lower stratum comprising an aqueous solution of acids which are predominantly formic acid and acetic acids.

4. The process of claim 3 wherein the liquid depth in each of said zones is between about 10 and about 30 feet.

5. The process of claim 4 wherein the liquid space in the first zone is greater than about 10 gallons per pound of BOD or COD which is added to the system per eight hours.

6. The process of claim 5 wherein the communication for liquid flow between the first and the second zones consists of an opening between said zones extending substantially from side to side of said zones and substantially from the bottoms of said zones to a height of about 30 inches above the bottom of said zones.

7. The process of claim 6 wherein said low solids aqueous suspension of organic waste solids has a solids content of less than about 3% by weight.

8. The process of claim 7 wherein the liquid depth in each of said zones is between about 10 and about 18 feet.

9. The process of claim 8 wherein said low solids aqueous suspension of organic waste solids has a solids content of about 2% by weight.

10. The process of claim 8 wherein solids passed from the second to the third zone are submerged upon entry into the third zone.

11. The process of claim 10 wherein said fourth and third anaerobic zones are about the same size as said first and second anaerobic zones, respectively.

12. The process of claim 11 wherein said fifth and sixth anaerobic zones are about the same size as said first and second anaerobic zones, respectively.

13. The process of claim 12 wherein the temperature of said six zones is maintained at less than 32° C.

14. The process of claim 13 further comprising periodically adding to said first zone one or more compositions selected from the group consisting of iron, copper sulfate and soluble molybdenum.

15. The process of claim 14 wherein the temperature of said six zones is maintained in the range of between about 26° C. and about 30° C.

16. The process of claim 15 wherein gas pressure above said six zones is maintained above atmospheric pressure.

* * * * *